US005451566A

United States Patent [19]

Mathews

[11] Patent Number: 5,451,566

[45] Date of Patent: Sep. 19, 1995

[54] HERBICIDAL PYRROLOPYRIDINE COMPOUNDS

[75] Inventor: Christopher J. Mathews, San Francisco, Calif.

[73] Assignee: Zeneca Limited, London, England

[21] Appl. No.: 153,702

[22] Filed: Nov. 17, 1993

[51] Int. Cl.[6] .................... A01N 43/40; C07D 471/02
[52] U.S. Cl. ..................... 504/246; 546/113
[58] Field of Search .................... 546/113; 504/246

[56]  References Cited

U.S. PATENT DOCUMENTS

| 5,023,265 | 6/1991 | Scherlock et al. | 514/300 |
| 5,120,782 | 6/1992 | Hübsch et al. | 514/300 |
| 5,167,691 | 12/1992 | Maravetz | 504/282 |
| 5,169,850 | 12/1992 | Dusza et al. | 514/258 |
| 5,169,947 | 12/1992 | Macor | 546/113 |
| 5,252,538 | 10/1993 | Cross et al. | 504/156 |
| 5,262,384 | 11/1993 | Hamprecht et al. | 504/225 |

FOREIGN PATENT DOCUMENTS

| 509717 | 10/1992 | European Pat. Off. |
| 031582 | 7/1971 | France |
| WO93/15049 | 8/1993 | WIPO |

OTHER PUBLICATIONS

"The synthesis of 5-azaindoles by substitution-rearrangement of 7-azaindoles upon treatment with certain primary amines", Journal of Heterocyclic Chemistry, vol. 26, pp. 317–325 (1989).

Chemical Abstracts, 77:48325b, "1H–Pyrazolo[3,4-b]-pyridines", Hoehn, H., J. Heterocycl. Chem., 1972, 9(2), pp. 235–253.

Derwent Abs. #83883 E/40 to EP 061056 (Sep. 29, 1992).

Primary Examiner—Glennon H. Hollrah
Assistant Examiner—Mary C. Cebulak
Attorney, Agent, or Firm—Marian T. Thomson

[57]  ABSTRACT

Herbicidal 1-aryl pyrrolopyridine compounds of the formula:

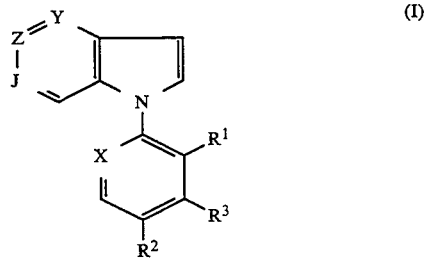

wherein at least one of Y, Z or J is N or N—O and the remainder of Y, Z or J is C—R.

47 Claims, No Drawings

HERBICIDAL PYRROLOPYRIDINE COMPOUNDS

FIELD OF THE INVENTION

In one aspect, this invention relates to novel pyrrolopyridine compounds which exhibit unexpectedly desirable herbicidal activity. In other aspects, this invention relates to herbicidal compositions comprising such pyrrolopyridine compounds and a suitable carrier, and to a method of controlling undesirable vegetation comprising applying to the area where control is desired an herbicidally effective amount of a pyrrolopyridine compound.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on noncropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide a novel herbicidal composition and a novel method of controlling weeds.

SUMMARY OF THE INVENTION

In one aspect, this invention is directed to a compound of the Formula (I):

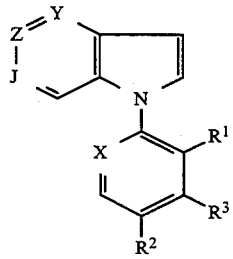

(I)

in which at least one of Y, Z or J is N or N—O and the remainder of Y, Z or J is C—R wherein R is hydrogen; halogen; cyano; $C_1$-$C_6$ alkyl; $C_1$-$C_6$ haloalkyl; $C_1$-$C_6$ alkoxy-$C_1$-$C_6$-alkyl; formyl; $C_1$-$C_6$ alkylcarbonyl; $C_1$-$C_6$ alkylcarbonyloxy; carboxy and its salts, esters and amides thereof; amino; substituted amino wherein the substituent(s) are selected from $C_1$-$C_6$ alkyl, $C_1$-$C_6$ alkoxy, hydroxy, formyl, $C_1$-$C_6$ alkylcarbonyl, $C_1$-$C_6$ alkoxycarbonyl, $C_1$-$C_6$ alkoxycarbonyl-$C_1$-$C_6$-alkylidenecarbonyl, hydroxycarbonyl-$C_1$-$C_6$-alkylidenecarbonyl, $C_1$-$C_6$ alkylsulfonyl, $C_1$-$C_6$ haloalkylsulfonyl, aminocarbonyl, (di)$C_1$-$C_6$-alkylaminocarbonyl, amino and (di)$C_1$-$C_6$-alkylamino; sulfonamido wherein the N is substituted with hydrogen and/or $C_1$-$C_6$ alkyl; $QR^5$ wherein Q is —O— or $S(O)_m$— and $R^5$ is selected from hydrogen, $C_1$-$C_6$ alkyl, $C_1$-$C_6$ haloalkyl, cyano-$C_1$-$C_6$-alkyl, $C_1$-$C_6$ alkoxycarbonyl-$C_1$-$C_6$-alkyl, $C_2$-$C_4$ alkenyl, $C_3$-$C_6$ alkynyl, hydroxycarbonyl-$C_1$-$C_6$-alkyl and aminocarbonyl-$C_1$-$C_6$-alkyl wherein the nitrogen atom may be optionally substituted with $C_1$-$C_6$ alkyl, $C_1$-$C_6$ alkoxy, $C_1$-$C_6$ alkylsulfonyl, $C_1$-$C_6$ haloalkylsulfonyl, amino or (di)$C_1$-$C_6$ alkylamino;

$R^1$ is hydrogen, nitro, halogen, cyano, $C_1$-$C_6$ alkyl-$S(O)_m$— or $C_1$-$C_6$ alkoxy;

$R^2$ is halogen, $C_1$-$C_6$ haloalkyl, cyano, or $C_1$-$C_6$ alkyl-$S(O)_m$—;

$R^3$ is hydrogen or halogen;

X is N or C—$R^4$;

wherein $R^4$ is hydrogen, $C_1$-$C_6$ haloalkyl, halogen, cyano, nitro, $C_1$-$C_6$ alkyl-$S(O)_m$— or $C_1$-$C_6$ alkoxy;

m is 0, 1, 2; and agriculturally acceptable salts thereof.

In another aspect, this invention is directed to a herbicidal composition comprising: (A) a compound of Formula (I) above and; (B) a carrier therefor.

In yet another aspect, this invention is directed to a method for controlling undesirable vegetation comprising applying to the area where control is desired an herbicidally effective amount of a compound of the Formula (I).

DETAILED DESCRIPTION OF THE PREFERRED EMBODIMENTS

The novel herbicidal compounds of this invention are the Formula (I):

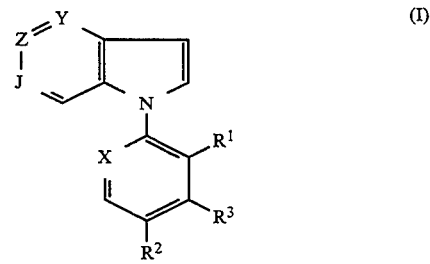

(I)

in which at least one of Y, Z or J is N or N—O and the remainder of Y, Z or J is C—R wherein R is hydrogen; halogen; cyano; $C_1$-$C_6$ alkyl; $C_1$-$C_6$ haloalkyl; $C_1$-$C_6$ alkoxy-$C_1$-$C_6$-alkyl; formyl; $C_1$-$C_6$ alkylcarbonyl; $C_1$-$C_6$ alkylcarbonyloxy; carboxy and its salts, esters and amides thereof; amino; substituted amino wherein the substituent(s) are selected from $C_1$-$C_6$ alkyl, $C_1$-$C_6$ alkoxy, hydroxy, formyl, $C_1$-$C_6$ alkylcarbonyl, $C_1$-$C_6$ alkoxycarbonyl, $C_1$-$C_6$ alkoxycarbonyl-$C_1$-$C_6$-alkylidenecarbonyl, hydroxycarbonyl-$C_1$-$C_6$-alkylidenecarbonyl, $C_1$-$C_6$ alkylsulfonyl, $C_1$-$C_6$ haloalkylsulfonyl, aminocarbonyl, (di)$C_1$-$C_6$-alkylaminocarbonyl, amino and (di)$C_1$-$C_6$-alkylamino; sulfonamido wherein the N is substituted with hydrogen and/or $C_1$-$C_6$ alkyl; $QR^5$ wherein Q is —O— or $S(O)_m$— and $R^5$ is selected from hydrogen, $C_1$-$C_6$ alkyl, $C_1$-$C_6$ haloalkyl, cyano-$C_1$-$C_6$-alkyl, $C_1$-$C_6$ alkoxycarbonyl-$C_1$-$C_6$-alkyl, $C_2$-$C_4$ alkenyl, $C_3$-$C_6$ alkynyl, hydroxycarbonyl-$C_1$-$C_6$-alkyl and aminocarbonyl-$C_1$-$C_6$-alkyl wherein the nitrogen atom may be optionally substituted with $C_1$-$C_6$ alkyl, $C_1$-$C_6$ alkoxy, $C_1$-$C_6$ alkylsulfonyl, $C_1$-$C_6$ haloalkylsulfonyl, amino or (di)$C_1$-$C_6$ alkylamino;

$R^1$ is hydrogen, nitro, halogen, cyano, $C_1$-$C_6$ alkyl-$S(O)_m$— or $C_1$-$C_6$ alkoxy;

$R^2$ is halogen, $C_1$–$C_6$ haloalkyl, cyano, or $C_1$–$C_6$ alkyl-S(O)$_m$—;

$R^3$ is hydrogen or halogen;

X is N or C—$R^4$;

wherein $R^4$ is hydrogen, $C_1$–$C_6$ haloalkyl, halogen, cyano, nitro, $C_1$–$C_6$ alkyl-S(O)$_m$— or $C_1$–$C_6$ alkoxy;

m is 0, 1, 2; and agriculturally acceptable salts thereof.

Preferably:

R is halogen; cyano; $C_1$–$C_6$ alkyl; $C_1$–$C_6$ haloalkyl; $C_1$–$C_6$ alkylcarbonyl; $C_1$–$C_6$ alkylcarbonyloxy; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; sulfonamido wherein the N is substituted with hydrogen and/or $C_1$–$C_6$ alkyl; QR$^5$ wherein Q is —O— or S(O)$_m$— and R$^5$ is selected from $C_1$–$C_6$ alkyl, $C_1$–$C_6$ haloalkyl, cyano-$C_1$–$C_6$-alkyl, $C_1$–$C_6$ alkoxycarbonyl-$C_1$–$C_6$-alkyl, $C_2$–$C_4$ alkenyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino;

$R^1$ is halogen, hydrogen, nitro, $C_1$–$C_6$ haloalkyl or $C_1$–$C_6$ alkyl-S(O)$_n$—, wherein n is 1 or 2;

$R^2$ is hydrogen, halogen, nitro, $C_1$–$C_6$ haloalkyl or $C_1$–$C_6$ alkyl-S(O)$_n$—, wherein n is 1 or 2;

$R^3$ is hydrogen; and $R^4$ is hydrogen, halogen or $C_1$–$C_6$ haloalkyl.

More preferably:

R is halogen; cyano; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$ -alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; QR$^5$ wherein Q is —O— or —S— and R$^5$ is selected from $C_1$–$C_6$ alkyl, cyano-$C_1$–$C_6$-alkyl, $C_1$–$C_6$ alkoxycarbonyl-$C_1$–$C_6$-alkyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino;

$R^1$ is chloro or fluoro;

$R^2$ is trifluoromethyl;

$R^3$ is hydrogen, and

X is N or C—H, C—Cl or C—F.

Particularly preferred compounds include:

4-chloro-1-(2-chloro-4-trifluoromethylphenyl)-pyrrolo[3,2-c]pyridine;

4-chloro-1-(2-chloro-4-trifluoromethylphenyl)-pyrrolo[3,2-c]pyridine 5-oxide;

1-(2-chloro-4-trifluoromethylphenyl)-4-methoxypyrrolo[3,2-c]pyridine;

4-chloro-1-(3'-chloro-5'-trifluoromethylpyridin-2'-yl)-pyrrolo [3,2-]pyridine;

4-chloro-1-(3'-chloro-5'-trifluoromethylpyridin-2-yl)-pyrrolo [3,2-c]pyridine, 5-oxide;

4-chloro-1-(2',6'-dichloro-4'-trifluoromethylphenyl)-pyrrolo [3,2-c]pyridine;

4-methoxy-1-(2,',6'-dichloro-4'-trifluoromethylphenyl)-pyrrolo [3,2-c]pyridine;

1-(2'-chloro-4'-trifluoromethylphenyl)-4-cyanopyrrolo [3,2-c]pyridine; and 1-(2',6'-dichloro-4'-trifluoromethylphenyl)-4-cyanopyrrolo[3,2-c]pyridine.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

The compounds of such formulae may exist in enantiomeric forms. The invention includes both individual enantiomers and mixtures of the two in all proportions.

The expression "salts, amides, and esters thereof" used above in relation to carboxy substitution includes, for example, salts formed from alkali metal (e.g., sodium, potassium, and lithium), alkaline earth metals (e.g., calcium and magnesium), the ammonium ion, and substituted ammonium ions wherein one, two, three, or four of the hydrogen atoms have been replaced by optionally substituted $C_{1-6}$ hydrocarbyl moieties. Such term preferably includes substituted carboxamido wherein such substituents are selected from $C_1$–$C_6$ alkyl, $C_1$–$C_6$ alkylsulfonyl and $C_1$–$C_6$ haloalkylsulfonyl.

As is employed herein, the term "alkyl" and all groups containing alkyl portions are intended to include straight chain, branched and cyclic groups. Examples include methyl, ethyl, n-propyl, isopropyl, cyclopropyl, n-butyl and t-butyl.

Further, in the above definitions the term "halogen" includes fluoro, chloro, bromo and iodo groups. In polyhalogenated groups the halogens may be the same or different. The term "haloalkyl" or the like refers to substituents having one or more halogen substituent.

The compounds of the present invention have been found to be active herbicides, possessing utility as pre-emergence and post-emergence herbicides and useful against a wide range of plant species including broadleaf and grassy species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes hydrohalogen, acetic, sulfonic, phosphonic, inorganic and organic acid salts.

In general, the compounds of this invention may be prepared by reacting a pyrrolopyridine of the formula:

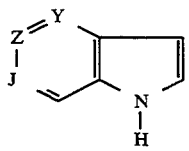

wherein J, Y and Z are as defined above, with substituted pyridine or benzene compound of the formula

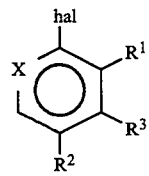

wherein hal is halogen; and X, $R^1$, $R^2$ and $R^3$, are as defined above; in the presence of a suitable base (such as a metal hydride or hydroxide or the like) in a suitable solvent (such as dimethyl sulfoxide, N,N-dimethylformamide or the like).

The pyrrolopyridine starting materials may be prepared by methods described in the literature, such as by R. E. Willette, *Advances in Heterocyclic Chemistry*, 9, 27 (1968); or I. Mahadevan and M. Rasmussen, *J. Heterocyclic Chem.*, 29, 359 (1992).

The halogenated pyridine or benzene starting materials are either commercially available or may be prepared by means well known to those of skill in the art.

Alternatively, the pyrrolopyridine compounds of this invention may be prepared by the cyclization of a preferred 1-arylpyrrole by a route analogous to the synthesis of pyrrolo [3,2-c]pyridines (5-azaindoles) from 1-benzylopyrrole described by C. Ducrocq et al., *Tetrahedron* 32, 773 (1976).

The compositions of this invention comprise a compound of Formula (I) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by pre-emergence or post-emergence application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplet are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. benzo-2,1,3-thiadiazin-4-one-2,2-dioxides such as bentazone;
B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);
C. 1,3-dimethylpyrazole derivatives such as pyrazoxyfen, pyrazolate and benzofenap;
D. dinitrophenols and their derivatives (e.g. acetates such as DNOC, dinoterb, dinoseb and its ester, dinoseb acetate);
E. dinitroaniline herbicides such as dinitramine, trifluralin, ethalfluralin, pendimethalin; and oryzalin;
F. arylurea herbicides such as diuron, flumeturon, metoxuron, neburon, isoproturon, chlorotoluron, chloroxuron, linuron, monolinuron, chlorobromuron, daimuron, and methabenzthiazuron;
G. phenylcarbamoyloxyphenylcarbamates such as phenmedipham and desmedipham;
H. 2-phenylpyridazin-3-ones such as chloridazon, and norflurazon;
I. uracil herbicides such as lenacil, bromacil and terbacil;
J. triazine herbicides such as atrazine, simazine, aziprotryne, cyanazine, prometryn, dimethametryn, simetryne, and terbutryn;
K. phosphorothioate herbicides such as piperophos, bensulide, and butamifos;
L. thiolcarbamate herbicides such as cycloate, vernolate, molinate, thiobencarb, butylate*, EPTC*, triallate, diallate, ethyl esprocarb, tiocarbazil, pyridate, and dimepiperate;

* These compounds are preferably employed in combination with a safener such as 2,2-dichloro-N,N-di-2-propenylacetamide (dichlormid).

M. 1,2,4-triazin-5-one herbicides such as metamitron and metribuzin;
N. benzoic acid herbicides such as 2,3,6-TBA, dicamba and chloramben;
O. anilide herbicides such as pretilachlor, butachlor, the corresponding alachlor, the corresponding compound propachlor, propanil, metazachlor, metolachlor, acetochlor, and dimethachlor;
P. dihalobenzonitrile herbicides such as dichlobenil, bromoxynil and ioxynil;
Q. haloalkanoic herbicides such as dalapon, TCA and salts thereof;
R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;
S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;
T. cyclohexanedione herbicides such as alloxydim and salts thereof, sethoxydim, cycloxydim, tralkoxydim, sulcotrione and clethodim;
U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;
V. imidazolidinone herbicides such as imazaquin, imazamethabenz, imazapyr and isopropylammonium salts thereof, imazethapyr;
W. arylanilide herbicides such as flamprop and esters thereof, benzoylprop-ethyl, diflufenican;
X. amino acid herbicides such as glyphosate and gluyfosinate and their salts and esters, sulphosate, and bilanafos;
Y. organoarsenical herbicides such as MSMA;
Z. herbicidal amide derivative such as napropamide, propyzamide, carbetamide, tebutam, bromobutide, isoxaben, naproanilide, diphenamid, and naptalam;
AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;
BB. examples of useful contact herbicides include bipyridylium herbicides such as those in which the active entity is paraquat and those in which the active entity is diquat.

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations. The following are examples of typical formulations.

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: | 5 parts active compound |
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| Wettable powders: | |
|---|---|
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25%: | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
|---|---|
| 25%: | 25 parts active substance |
| | 2.5 parts epoxidized vegetable oil |
| | 10 parts of an alkylarylsulfonate/fatty |

| Emulsifiable concentrate: | |
|---|---|
| | alcohol polyglycol ether mixture |
| | 5 parts dimethylformamide |
| | 57.5 parts xylene |

The amount of the present compositions which constitute a herbicidally effective amount depends upon the nature of the seeds or plants to be controlled. The rate of application of active ingredients varies from about 0.01 to about 25 pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following Examples are intended to further illustrate the present invention and are not intended to limit the scope of this invention in any manner whatsoever.

EXAMPLE 1

Preparation of 1-(3'-chloro-5'-trifluoromethylpyridin-2-yl)-pyrrolo[2,3-c]pyridine (Compound No. 1)

Step 1

N,N-dimethylformamide dimethyl acetal (10 ml) and pyrrolidine (3 ml) were added to a solution of 3-nitro-4-methylpyridine (5.0 g, 36 mmol) in N,N-dimethylformamide (50 ml) and the mixture heated to 120° C. for 2 hours. The mixture was cooled to room temperature and partitioned between diethyl ether and water. The ethereal extract was dried over magnesium sulfate, filtered and the filtrate evaporated to give a deep red solid, used directly without further purification in the next step.

Step 2

The mixture of nitro-enamines obtained in Step 1 (3.8 g) was hydrogenated at 40 p.s.i. over palladium on charcoal catalyst (0.4 g) in ethanol (125 ml) for 1 hour and 30 minutes. The catalyst was removed by filtration, the filtrate evaporated and the residue purified by flash column chromatography on silica gel (20% methanol in ethyl acetate) to give 1H-pyrrolo[3,2-c]pyridine (6-azaindole) as a pale yellow solid.

Step 3

1H-pyrrolo[2,3-c]pyridine (1.0 g, 8 mmol) was added to a suspension of sodium hydride (80% dispersion in oil, 0.5 g, 17 mmol) and the mixture stirred at room temperature overnight. 2,3-dichloro-5-trifluoromethylpyridine (1.7 g, 8 mmol) was added, and the mixture stirred at room temperature overnight. The mixture was partitioned between diethyl ether and water. The ethereal extract was dried over magnesium sulfate, filtered and the filtrate evaporated to give, 1-(3-chloro-5-trifluoromethylpyridin-2-yl)-pyrrolo[2,3-c]pyridine (1.4 g) as a yellow solid, m.p. 88°–90° C.

EXAMPLE 2

Preparation of 4-chloro-1-(2'-chloro-4'-trifluoromethylphenyl)-pyrrolo[3,2-c]pyridine (Compound No. 3)

Step 1

A solution of pyrrole-2-carboxaldehyde (19.0 g, 0.2 mol) in N,N-dimethylformamide (50 ml) was added dropwise to a suspension of sodium hydride (80% dispersion in oil, 6.3 g, 0.21 mol) in N,N-dimethylformamide (100 ml), maintaining the temperature of the reaction between 5°–10° C. by means of ice-bath cooling. When the addition was complete, stirring was continued for 30 minutes, and then 3-chloro-4-fluorobenzotrifluoride (39.7 g, 0.20 mol) added. The mixture was stirred for 3 hours, then warmed to 50° C. for 18 hours. The mixture was cooled to room temperature and partitioned between diethyl ether and water. The ethereal extract was washed sequentially with water and brine, dried over magnesium sulfate, filtered and the filtrate evaporated. Trituration with hexane gave 1-(2'-chloro-4'-trifluoromethylphenyl)pyrrole-2-carboxaldehyde as a pale yellow solid (30.6 g), m.p. 119°–120° C.

Step 2

A mixture of the aldehyde prepared in Step 1 above (29.5 g, 0.11 mol) and carboethoxymethylene triphenylphosphorane (45.0 g, 0.13 mol) were heated together in refluxing toluene for 15 hours. The mixture was cooled to room temperature, and most of the solvent removed in vacuo. Hexane (400 ml) was added and the precipitated solids removed by filtration. The filtrate was evaporated to give a red-brown oil used without further purification in the next step.

Step 3

A solution of sodium hydroxide (8.8 g, 0.22 mol) in water (100 ml) was added to a solution of the ester prepared in Step 2 above in isopropanol (300 ml), and the mixture heated to reflux for 3 hours. Most of the solvent was evaporated in vacuo, and water added. The mixture was partitioned with diethyl ether, and aqueous phase collected and acidified to pH 1. The precipitate was collected and dried to give 3-(1-[2'-chloro-4'-trifluoromethylphenyl]pyrrole-2-)-acrylic acid (27.4 g) as a colorless solid, m.p. 209°–211° C.

Step 4

Ethyl chloroformate (7.16 g, 5.3 ml, 66 mmol) was added dropwise to a mixture of triethylamine (6.68 g, 9.2 ml, 66 mmol) and the acid prepared above (19.0 g, 60 mmol) in acetone, keeping the reaction mixture below 10° C. by means of external ice-bath cooling, and the mixture was stirred for 1 hour. To this cooled mixture was added, dropwise, a solution of sodium azide (4.29 g, 66 mmol) in water (40 ml), and stirring was continued for a further 1 hour. The mixture was poured into water and extracted with dichloromethane. The organic extract was dried over magnesium sulfate, filtered, and the filtrate used directly in the next step.

Step 5

The solution of the acyl azide, prepared in Step 4 above, in dichloromethane, was added dropwise to a mixture of tributylamine (11.1 g, 14.3 ml, 60 mmol) and diphenyl ether (190 ml) at 195°–205° C.; the rate of addition was such that the dichloromethane could be collected by distillation without the temperature of the reaction mixture falling below 195° C. Once the addition was complete, the mixture was cooled to room temperature, hexane (800 ml) was added and the mixture stirred overnight. The precipitate was collected and washed with hexane to give 1-(2'-chloro-4'-trifluoromethylphenyl)-4,5-dihydro-4-oxopyrrolo[3,2-c]pyridine (10.9 g). A small portion was further purified by dissolution in chloroform, followed by precipitation by addition of toluene, to give the oxopyrrolo[3,2-c]pyridine as a colorless solid, m.p. 233°–235° C.

Step 6

The oxopyrrolo[3,2-c]pyridine (8.0 g, 26 mmol) prepared above and phosphorus oxychloride (80 ml) were heated together under reflux for 3 hours, then cooled to room temperature. Most of the solvent was removed in vacuo, and the residue poured onto ice-water. Solid sodium carbonate was added until the mixture reached pH 7, then the mixture was extracted with diethyl ether. The organic extract was dried over magnesium sulfate, filtered and the filtrate evaporated. The residue was taken up in boiling hexane, once more filtered, and the filtrate evaporated to give, 4-chloro-1-(2'-chloro-4'-trifluoromethylphenyl)-pyrrolo[3,2-c]pyridine (5.5 g) as a pale yellow solid, m.p. 133°–135° C.

EXAMPLE 3

Production of 4-chloro-1-(2'-chloro-4'-trifluoromethylphenyl)-pyrrolo[3,2-c]pyridine 5-oxide (Compound No. 9)

4-chloro-1-(2'-chloro-4'-trifluoromethylphenyl)-pyrrolo[3,2-c]pyridine (1.10 g, 33 mmol) and meta-chloroperbenzoic acid (approximately 80–85%, 1.15 g) were stirred together in chloroform (20 ml) at room temperature overnight. A further quantity of meta-chloroperbenzoic acid (1.15 g) was added, and stirring continued for 2 hours. The mixture was diluted with dichloromethane and washed with saturated aqueous sodium carbonate solution. The organic portion was dried over magnesium sulfate, filtered, and the filtrate evaporated in vacuo. The residue was triturated with hexane to give 4-chloro-1-(2'-chloro-4'-trifluoromethylphenyl)-pyrrolo[3,2-c]-pyridine 5-oxide (0.69 g) as a tan solid, m.p. 119°–123° C. (with dec.)

EXAMPLE 4

Production of 1-(2'-chloro-4'-trifluoromethylphenyl)-4-methoxy-pyrrolo[3,2-c]pyridine (Compound No. 7)

Potassium hydroxide (0.7 g, 12 mmol) and methanol (2 ml) were stirred together in dimethyl sulfoxide (20 ml) at room temperature for 30 minutes. 4-chloro-1-(2-chloro-4-trifluoromethylphenyl)-pyrrolo[3,2-c]pyridine (2.0 g, 6 mmol) was added and stirring continued for 18 hours. The mixture was poured into water and the precipitate collected by filtration. Further purification by flash column chromatography on silica gel gave 1-(2'-chloro-4'-trifluoromethylphenyl)-4-methoxy-pyrrolo[3,2-c]pyridine (0.35 g) as a pale yellow solid, m.p. 112°–115° C.

EXAMPLE 5

Production of 1-(2-chloro-4-trifluoromethylphenyl)-4-cyano-pyrrolo[3,2-c]pyridine (Compound No. 13)

A solution of 1-(2-chloro-4-trifluoromethylphenyl)-pyrrolo[3,2-c]pyridine 5-oxide (3.5 g, 12 mmol) in triethylamine (50 ml) was cooled in an ice-bath and trimethylsilyl cyanide (10.7 ml, 80 mmol) added dropwise. The ice-bath was removed and the mixture stirred for 5 hours. The precipitate was collected and dried to afford 1-(2-chloro-4-trifluoromethylphenyl)pyrrolo[3,2-c]pyridine (1.8g) as a colorless solid, m.p. 160°–161° C.

EXAMPLE 6

Production of 1-(3-chloro-5-trifluoromethylpyridin-2-yl)-4,6-dichloropyrrolo[3,2-c]pyridine (Compound No. 16)

4-chloro-1-(3-chloro-5-trifluoromethylpyridin-2-yl) pyrrolo[3,2-c]pyridine N-oxide (Compound 4, 1.2 g, 3.4 mmol) was heated in phosphorus oxychloride (20 ml) under reflux for 18 hours. The mixture was cooled to room temperature, poured into ice-water, and the mixture made neutral by addition of solid sodium bicarbonate. The resulting mixture was extracted with dichloromethane, and the organic extracts combined, dried over magnesium sulfate, filtered and the filtrate evaporated in vacuo. The residue was further purified by flash column chromatography on silica gel to give 1-(3-chloro-5-trifluoromethylpyridin-2-yl)-4,6-dichloropyrrolo[3,2-c]pyridine (0.24 g) as a colorless oil.

EXAMPLE 7

Employing processes similar to those described above, the following compounds, listed in Table I, were prepared:

TABLE I

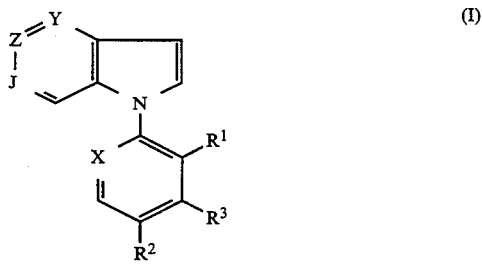

(I)

| Comp. No. | R$^1$ | R$^2$ | R$^3$ | X | J | Y | Z |
|---|---|---|---|---|---|---|---|
| 1 | Cl | —CF$_3$ | H | N | N | —CH | —CH |
| 2 | Cl | —CF$_3$ | H | N | —CH | —CCl | N |
| 3 | Cl | —CF$_3$ | H | —CH | —CH | —CCl | N |
| 4 | Cl | —CF$_3$ | H | N | —CH | —CCl | N$^+$—O$^-$ |
| 5 | Cl | —CF$_3$ | H | —CCl | —CH | —CCl | N |
| 6 | Cl | —CF$_3$ | H | —CCl | —CH | —COCH$_3$ | N |
| 7 | Cl | —CF$_3$ | H | —CH | —CH | —COCH$_3$ | N |
| 8 | Cl | —CF$_3$ | H | N | —CH | —CH | N |
| 9 | Cl | —CF$_3$ | H | —CH | —CH | —CCl | N$^+$—O$^-$ |
| 10 | Cl | —CF$_3$ | H | —CH | —CH | —CH | N |
| 11 | Cl | —CF$_3$ | H | —CH | —CH | —CH | N$^+$—O$^-$ |
| 12 | Cl | —CF$_3$ | H | —CCl | —CH | —CH | N |
| 13 | Cl | —CF$_3$ | H | —CH | —CH | —C—C=N | N |
| 14 | Cl | —CF$_3$ | H | —CCl | —CH | —C—C=N | N |
| 15 | Cl | —CF$_3$ | H | —CH | —CH | —C—C=N | N$^+$—O$^-$ |
| 16 | Cl | —CF$_3$ | H | N | —CCl | —CCl | N |

HERBICIDAL SCREENING TESTS

The compounds listed in the foregoing table were tested for herbicidal activity by various methods and at various rates of application. The results of some of these tests are given below. Results obtained in herbicidal screening are affected by a number of factors including: the amount of sunlight, soil type, soil pH, temperature, humidity, depth of planting, plant growth stage, application rate as well as many other factors. All testing procedures are administered with the least amount of variability possible. State of the art equipment and techniques are employed to enable the screening process to remain consistent and reliable.

PRE-EMERGENCE HERBICIDAL SCREENING TEST

On the day preceding treatment, seeds of several different weed species were planted in sandy loam soil containing only trace organic matter. Propagules were sown in individual rows using one species per row across the width of an aluminum flat (19.5×9.5×6 cm). The grass weeds planted were green foxtail (*Setaria viridis*) ("SETVI"), wild oat (*Avena fatua*) ("AVEFA"), barnyardgrass (*Echinochloa crusgalli*) ("ECHCG"). Broadleaf weeds utilized were wild mustard (*Brassica kaber*) also known as (*Sinatis Arvensis*) ("SINAR"), velvetleaf (*Abutilon theophrasti*) ("ABUTH") and morningglory (Ipomoea spp.) ("IPOSS"). Additionally, yellow nutsedge (*Cyperus esculentus*) ("CYPES"), nutlets were sown. Seeding depths ranged from 1.0 to 1.5 cm and plant densities ranged from 3 to 25 plants per row depending on individual plant species.

Solutions of the test compounds were prepared by weighing out 74.7 mg of the test compound into a 60 ml wide-mouth bottle, then dissolving the compound in 7.0 ml of acetone containing 1% v/v Tween 20 ® (polyoxyethylene sorbitan monolaurate emulsifier) as a surfactant and then adding 7 ml of deionized water to reach a 14 ml final volume. Tween 20 ® content was 0.5% v/v of the final spray volume. Additional solvents, not exceeding 2 ml (15% of spray volume), were used if needed to dissolve the compound.

The soil surface was sprayed inside an enclosed linear spray table with the nozzle set at 30.5 cm (12 inches) above the soil line. The spray table was calibrated to deliver 748 L/ha (80 gal/A) with the application rate being 4.0 kg/ha or 1.0 kg/ha (as indicated in Table II below). After treatment the flats were placed into a greenhouse and watered overhead by sprinkling. The greenhouse environmental systems provided the plants with natural and artificial (via metal halide lamps) lighting to attain 14 hours of light per day. Day and night temperatures were maintained at 29° and 21° C. respectively.

The degree of week control was evaluated and recorded 17-21 days after treatment as a percentage of weed control as compared to the growth of the same species of the same age in an untreated control flat. Percent control is the total injury to the plants due to all factors including: inhibited emergence, stunting, malformation, chlorosis and other types of plant injury. The control ratings range from 0 to 100 percent, where 0% represents no effect with growth equal to the untreated control and where 100% represents complete kill. A dash indicates that no test was performed at that level of application.

POST-EMERGENCE HERBICIDAL EVALUATION

The soil was prepared and seeded with the same species and methodology described for the pre-emergence test. Post-emergence flats were placed in the greenhouse under the same environmental conditions as described for the pre-emergence flats and watered overhead by sprinkling. Plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Plants were sprayed 30.5 cm (12 inches) above the foliage with the same spray solution as prepared for the pre-emergence test. The application rate was 4.0 kg/ha or 1.0 kg/ha (as indicated in Table III below). Treated plants were then returned to a greenhouse and watered daily without wetting the foliage. The degree of weed control was evaluated 17-21 days after application and recorded as percentage of control as compared to the growth of the same species in an untreated control flat of the same age. The percent control scale (0-100%) used to evaluate the pre-emergence treatment was also applied to the post-emergence treatment.

TABLE II

| COMP. NO. | Pre-Emergent - Testing (1.0 kg/ha) | | | | | | |
|---|---|---|---|---|---|---|---|
| | AVEFA | ECHCG | SETVI | ABUTH | IPOSS | SINAR | CYPES |
| 1* | 0 | 0 | 10 | 10 | 0 | 3 | 0 |
| 2* | 100 | 100 | 100 | 100 | 100 | 100 | 60 |
| 3 | 100 | 100 | 100 | 100 | 100 | 100 | 10 |
| 4 | 20 | 95 | 100 | 100 | 40 | 50 | 75 |
| 5 | 98 | 100 | 100 | 100 | 100 | 100 | 10 |
| 6 | 75 | 85 | 100 | 100 | 100 | 100 | 5 |
| 7 | 25 | 40 | 100 | 70 | 100 | 100 | 0 |
| 8 | 15 | 15 | 100 | 20 | 5 | 5 | 5 |
| 9 | 15 | 95 | 100 | 100 | 100 | 100 | 30 |
| 10 | 0 | 0 | 5 | 10 | 5 | 0 | 0 |
| 11 | 0 | 0 | 5 | 10 | 10 | 0 | 0 |
| 12 | 0 | 0 | 5 | 30 | 85 | 0 | 0 |
| 13 | 50 | 100 | 100 | 100 | 80 | 100 | 5 |
| 14 | 40 | 100 | 100 | 100 | 30 | 100 | 5 |
| 15 | 40 | 98 | 100 | 100 | 25 | 98 | 60 |
| 16 | 100 | 100 | 100 | 100 | 75 | 100 | 40 |

*Tested at 4.0 kg/ha

TABLE III

| COMP. NO. | Pre-Emergent - Testing (1.0 kg/ha) | | | | | | |
|---|---|---|---|---|---|---|---|
| | AVEFA | ECHCG | SETVI | ABUTH | IPOSS | SINAR | CYPES |
| 1* | 5 | 5 | 30 | 95 | 45 | 20 | 0 |
| 2* | 100 | 100 | 100 | 100 | 100 | 100 | 70 |
| 3 | 100 | 100 | 100 | 100 | 100 | 100 | 30 |
| 4 | 85 | 100 | 100 | 100 | 100 | 90 | 70 |
| 5 | 100 | 100 | 100 | 100 | 100 | 100 | 30 |
| 6 | 100 | 100 | 100 | 100 | 100 | 100 | 15 |
| 7 | 100 | 100 | 100 | 100 | 100 | 90 | 25 |
| 8 | 60 | 100 | 100 | 100 | 100 | 90 | 15 |
| 9 | 100 | 100 | 100 | 100 | 100 | 100 | 50 |
| 10 | 0 | 5 | 5 | 60 | 20 | 0 | 0 |
| 11 | 0 | 0 | 10 | 75 | 10 | 5 | 0 |
| 12 | 5 | 15 | 15 | 100 | 98 | 20 | 0 |
| 13 | 100 | 85 | 100 | 100 | 100 | 100 | 10 |
| 14 | 100 | 100 | 100 | 100 | 100 | 100 | 15 |
| 15 | 60 | 100 | 100 | 100 | 100 | 100 | 10 |
| 16 | 100 | 100 | 100 | 100 | 100 | 100 | 20 |

*Tested at 4.0 kg/ha

The results above illustrate the preemergent and postemergent efficacy of the present compounds against a variety of grasses and broadleaf species.

What is claimed is:

1. A compound of the formula

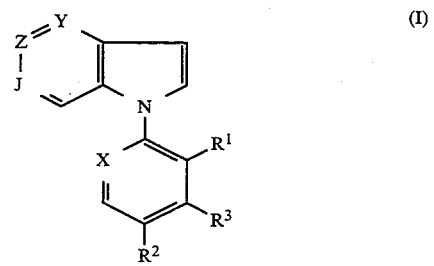

in which only one of Y, Z or J is N or N—O and the remainder of Y, Z or J is C—R wherein R is hydrogen; halogen; cyano; $C_1$-$C_6$ haloalkyl; $C_1$-$C_6$ alkoxy-$C_1$-$C_6$-alkyl; formyl; $C_1$-$C_6$ alkylcarbonyl; $C_1-C_6$ alkylcarbonyloxy; carboxy and its salts, esters and amides thereof; amino; substituted amino wherein the substituent(s) are selected from $C_1-C_6$ alkyl, $C_1-C_6$ alkoxy, hydroxy, formyl, $C_1-C_6$ alkylcarbonyl, $C_1-C_6$ alkoxycarbonyl, $C_1-C_6$ alkoxycarbonyl-$C_1-C_6$-alkylidenecarbonyl, hydroxycarbonyl-$C_1-C_6$-alkylidenecarbonyl, $C_1-C_6$ alkylsulfonyl, $C_1-C_6$ haloalkylsulfonyl, aminocarbonyl, (di)$C_1-C_6$-alkylaminocarbonyl, amino and (di)$C_1-C_6$-alkylamino; sulfonamido wherein the N is substituted with hydrogen or $C_1-C_6$ alkyl; $QR^5$ wherein Q is —O— or $S(O)_m$— and $R^5$ is selected from hydrogen, $C_1-C_6$ alkyl, $C_1-C_6$ haloalkyl, cyano-$C_1-C_6$-alkyl, $C_1-C_6$ alkoxycarbonyl-$C_1-C_6$-alkyl, $C_2-C_4$ alkenyl, $C_3-C_6$ alkynyl, hydroxycarbonyl-$C_1-C_6$-alkyl and aminocarbonyl-$C_1-C_6$-alkyl wherein the nitrogen atom may be optionally substituted with $C_1-C_6$ alkyl, $C_1-C_6$ alkoxy, $C_1-C_6$ alkylsulfonyl, $C_1-C_6$ haloalkylsulfonyl, amino or (di)$C_1-C_6$ alkylamino;

$R^1$ is hydrogen, nitro, halogen, cyano, $C_1-C_6$ alkyl-$S(O)_m$— or $C_1-C_6$ alkoxy;

$R^2$ is halogen, $C_1-C_6$ haloalkyl, cyano, or $C_1-C_6$ alkyl-$S(O)_m$—;

$R^3$ is hydrogen or halogen;

X is N or C—$R^4$;

wherein $R^4$ is hydrogen, $C_1-C_6$ haloalkyl, halogen, cyano, nitro, $C_1-C_6$ alkyl-$S(O)_m$— or $C_1-C_6$ alkoxy;

m is 0, 1, 2; and agriculturally acceptable salts thereof.

2. A compound in accordance with claim 1 wherein R is halogen; cyano; $C_1-C_6$ alkyl; $C_1-C_6$ haloalkyl; $C_1-C_6$ alkylcarbonyl; $C_1-C_6$ alkylcarbonyloxy; substituted amino wherein the substituent(s) are selected from $C_1-C_6$ alkyl, $C_1-C_6$ alkoxy, hydroxy, formyl, $C_1-C_6$ alkylcarbonyl, $C_1-C_6$ alkoxycarbonyl, $C_1-C_6$ alkoxycarbonyl-$C_1-C_6$-alkylidenecarbonyl, hydroxycarbonyl-$C_1-C_6$-alkylidenecarbonyl, $C_1-C_6$ alkylsulfonyl, $C_1-C_6$ haloalkylsulfonyl, aminocarbonyl, (di)$C_1-C_6$-alkylaminocarbonyl, amino and (di)$C_1-C_6$-alkylamino; sulfonamido wherein the N is substituted with hydrogen or $C_1-C_6$ alkyl; $QR^5$ wherein Q is —O— or $S(O)_m$— and $R^5$ is selected from $C_1-C_6$ alkyl, $C_1-C_6$ haloalkyl, cyano-$C_1-C_6$-alkyl, $C_1-C_6$ alkoxycarbonyl-$C_1-C_6$-alkyl, $C_2-C_4$ alkenyl, $C_3-C_6$ alkynyl, hydroxycarbonyl-$C_1-C_6$-alkyl and aminocarbonyl-$C_1-C_6$-alkyl wherein the nitrogen atom may be optionally substituted with $C_1-C_6$ alkyl, $C_1-C_6$ alkoxy, $C_1-C_6$ alkylsulfonyl, $C_1-C_6$ haloalkylsulfonyl, amino or (di)$C_1-C_6$-alkylamino.

3. A compound in accordance with claim 2 wherein R is halogen; cyano; substituted amino wherein the substitutent(s) are selected from $C_1-C_6$ alkyl, $C_1-C_6$ alkoxy, hydroxy, formyl, $C_1-C_6$ alkylcarbonyl, $C_1-C_6$ alkoxycarbonyl, $C_1-C_6$ alkoxycarbonyl-$C_1-C_6$-alkylidenecarbonyl, hydroxycarbonyl-$C_1-C_6$-alkylidenecarbonyl, $C_1-C_6$ alkylsulfonyl, $C_1-C_6$ haloalkylsulfonyl, aminocarbonyl, (di)$C_1-C_6$-alkylaminocarbonyl, amino and (di)$C_1-C_6$-alkylamino; $QR^5$ wherein Q is —O— or —S— and $R^5$ is selected from $C_1-C_6$ alkyl, cyano-$C_1-C_6$-alkyl, $C_1-C_6$ alkoxycarbonyl-$C_1-C_6$-alkyl, $C_3-C_6$ alkynyl, hydroxycarbonyl-$C_1-C_6$-alkyl and aminocarbonyl-$C_1-C_6$-alkyl wherein the nitrogen atom may be optionally substituted with $C_1-C_6$ alkyl, $C_1-C_6$ alkoxy, $C_1-C_6$ alkylsulfonyl, $C_1-C_6$ haloalkylsulfonyl, amino or (di)$C_1-C_6$-alkylamino.

4. A compound in accordance with claim 1 wherein $R^1$ is chloro or fluoro;

$R^2$ is trifluoromethyl;

$R^3$ is hydrogen, and

X is N or C—H, C—Cl or C—F.

5. A compound in accordance with claim 1 wherein R is halogen; cyano; $C_1-C_6$ alkyl; $C_1-C_6$ haloalkyl; $C_1-C_6$ alkylcarbonyl; $C_1-C_6$ alkylcarbonyloxy; substituted amino wherein the substituent(s) are selected from $C_1-C_6$ alkyl, $C_1-C_6$ alkoxy, hydroxy, formyl, $C_1-C_6$ alkylcarbonyl, $C_1-C_6$ alkoxycarbonyl, $C_1-C_6$ alkoxycarbonyl-$C_1-C_6$-alkylidenecarbonyl, hydroxycarbonyl-$C_1-C_6$-alkylidenecarbonyl, $C_1-C_6$ alkylsulfonyl, $C_1-C_6$ haloalkylsulfonyl, aminocarbonyl, (di)$C_1-C_6$-alkylaminocarbonyl, amino and (di)$C_1-C_6$-alkylamino; sulfonamido wherein the N is substituted with hydrogen or $C_1-C_6$ alkyl; $QR^5$ wherein Q is —O— or $S(O)_m$— and $R^5$ is selected from $C_1-C_6$ alkyl, $C_1-C_6$ haloalkyl, cyano-$C_1-C_6$-alkyl, $C_1-C_6$ alkoxycarbonyl-$C_1-C_6$-alkyl, $C_2-C_4$ alkenyl, $C_3-C_6$ alkynyl, hydroxycarbonyl-$C_1-C_6$-alkyl and aminocarbonyl-$C_1-C_6$-alkyl wherein the nitrogen atom may be optionally substituted with $C_1-C_6$ alkyl, $C_1-C_6$ alkoxy, $C_1-C_6$ alkylsulfonyl, $C_1-C_6$ haloalkylsulfonyl, amino or (di)$C_1-C_6$-alkylamino;

$R^1$ is halogen, hydrogen, nitro, $C_1-C_6$ haloalkyl or $C_1-C_6$ alkyl-$S(O)_n$—, wherein n is 1 or 2;

$R^2$ is halogen, hydrogen, nitro, $C_1-C_6$ haloalkyl or $C_1-C_6$ alkyl-$S(O)_n$—, wherein n is 1 or 2;

$R^3$ is hydrogen; and $R^4$ is hydrogen, halogen or $C_1-C_6$ haloalkyl.

6. A compound in accordance with claim 1 wherein R is halogen; cyano; substituted amino wherein the substitutent(s) are selected from $C_1-C_6$ alkyl, $C_1-C_6$ alkoxy, hydroxy, formyl, $C_1-C_6$ alkylcarbonyl, $C_1-C_6$ alkoxycarbonyl, $C_1-C_6$ alkoxycarbonyl-$C_1-C_6$-alkylidenecarbonyl, hydroxycarbonyl-$C_1-C_6$-alkylidenecarbonyl, $C_1-C_6$ alkylsulfonyl, $C_1-C_6$ haloalkylsulfonyl, aminocarbonyl, (di)$C_1-C_6$-alkylaminocarbonyl, amino and (di)$C_1-C_6$-alkylamino; $QR^5$ wherein Q is —O— or —S— and $R^5$ is selected from $C_1-C_6$ alkyl, cyano-$C_1-C_6$-alkyl, $C_1-C_6$ alkoxycarbonyl-$C_1-C_6$-alkyl, $C_3-C_6$ alkynyl, hydroxycarbonyl-$C_1-C_6$-alkyl and aminocarbonyl-$C_1-C_6$-alkyl wherein the nitrogen atom may be optionally substituted with $C_1-C_6$ alkyl, $C_1-C_6$ alkoxy, $C_1-C_6$ alkylsulfonyl, $C_1-C_6$ haloalkylsulfonyl, amino or (di)$C_1-C_6$-alkylamino;

$R^1$ is chloro or fluoro;

$R^2$ is trifluoromethyl;

$R^3$ is hydrogen, and

X is N or C—H, C—Cl or C—F.

7. A compound in accordance with claim 1 wherein said compound is 4-chloro-1-(2-chloro-4-trifluoromethylphenyl)-pyrrolo [3,2-c]pyridine.

8. A compound in accordance with claim 1 wherein said compound is 4-chloro-1-(2-chloro-4-trifluoromethylphenyl)pyrrolo [3,2-c]pyridine 5-oxide.

9. A compound in accordance with claim 1 wherein said compound is 1-(2-chloro-4-trifluoromethylphenyl)-4-methoxy-pyrrolo [3,2-c]pyridine.

10. A compound in accordance with claim 1 wherein said compound is 4-chloro-1-(3'-chloro-5'-trifluoromethylpyridin-2'-yl)-pyrrolo [3,2-c]pyridine.

11. A compound in accordance with claim 1 wherein said compound is 4-chloro-1-(3'-chloro-5'-trifluoromethylpyridin-2-yl)-pyrrolo [3,2-c]pyridine 5-oxide.

12. A compound in accordance with claim 1 wherein said compound is 4-chloro-1-(2', 6'-dichloro-4'-trifluoromethylphenyl)-pyrrolo [3,2-c]pyridine.

13. A compound in accordance with claim 1 wherein said compound is 4-methoxy-1-(2,',6'-dichloro-4'-trifluoromethylphenyl)-pyrrolo [3,2-c]pyridine.

14. A compound in accordance with claim 1 wherein said compound is 1-(2'-chloro-4'-trifluoromethylphenyl)-4-cyanopyrrolo [3,2-c]pyridine.

15. A compound in accordance with claim 1 wherein said compound is 1-2',6'-dichloro-4 '-trifluoromethylphenyl)-4-cyanopyrrolo [3,2-c]pyridine.

16. A herbicidal composition comprising
(A) a compound of the formula:

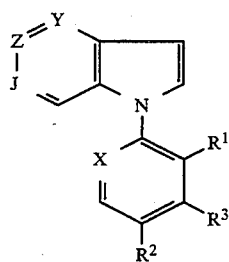

(I)

in which only one of Y, Z or J is N—O and the remainder of Y, Z or J is C—R wherein R is hydrogen; halogen; cyano; $C_1$–$C_6$ alkyl; $C_1$–$C_6$ haloalkyl; $C_1$–$C_6$ alkoxy-$C_1$–$C_6$-alkyl; formyl; $C_1$–$C_6$ alkylcarbonyl; $C_1$–$C_6$ alkylcarbonyloxy; carboxy and its salts, esters and amides thereof; amino; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; sulfonamido wherein the N is substituted with hydrogen or $C_1$–$C_6$ alkyl; $QR^5$ wherein Q is —O— or S(O)$_m$— and $R^5$ is selected from hydrogen, $C_1$–$C_6$ alkyl, $C_1$–$C_6$ haloalkyl, cyano-$C_1$–$C_6$-alkyl, $C_1$–$C_6$ alkoxycarbonyl-$C_1$–$C_6$-alkyl, $C_2$–$C_4$ alkenyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$ alkylamino;

$R^1$ is hydrogen, nitro, halogen, cyano, $C_1$–$C_6$ alkyl-S(O)$_m$—or $C_1$–$C_6$ alkoxy;

R'is halogen, $C_1$–$C_6$ haloalkyl, cyano, or $C_1$–$C_6$ alkyl-S(O)$_m$—;

$R^3$ is hydrogen or halogen;

X is N or C—$R^4$;

wherein $R^4$ is hydrogen, $C_1$–$C_6$ haloalkyl, halogen, cyano, nitro, $C_1$–$C_6$ alkyl-S(O)$_m$—or $C_1$–$C_6$ alkoxy;

m is 0, 1, 2; and agriculturally acceptable salts thereof and (B) an agriculturally acceptable carrier therefor.

17. A composition in accordance with claim 16 wherein

R is halogen; cyano; $C_1$–$C_6$ alkyl; $C_1$–$C_6$ haloalkyl; $C_1$–$C_6$ alkylcarbonyl; $C_1$–$C_6$ alkylcarbonyloxy; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino, and (di)$C_1$–$C_6$-alkylamino; sulfonamido wherein the N is substituted with hydrogen or $C_1$–$C_6$ alkyl; $QR^5$ wherein Q is —O— or S(O)$_m$— and $R^5$ is selected from $C_1$–$C_6$ alkyl, $C_1$–$C_6$ haloalkyl, cyano-$C_1$–$C_6$-alkyl, $C_1$–$C_6$ alkoxycarbonyl-$C_1$–$C_6$-alkyl, $C_2$–$C_4$ alkenyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino.

18. A composition in accordance with claim 17 wherein

R is halogen; cyano; substituted amino wherein the substitutent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; $QR^5$ wherein Q is —O— or —S— and $R^5$ is selected from $C_1$–$C_6$ alkyl, cyano-$C_1$–$C_6$-alkyl, $C_1$–$C_6$ alkoxycarbonyl-$C_1$–$C_6$-alkyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino.

19. A composition in accordance with claim 16 wherein $R^1$ is chloro or fluoro;

$R^2$ is trifluoromethyl;

$R^3$ is hydrogen, and

X is N or C—H, C—Cl or C—F.

20. A composition in accordance with claim 16 wherein

R is halogen; cyano; $C_1$–$C_6$ alkyl; $C_1$–$C_6$ haloalkyl; $C_1$–$C_6$ alkylcarbonyl; $C_1$–$C_6$ alkylcarbonyloxy; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino, and (di)$C_1$–$C_6$-alkylamino; sulfonamido wherein the N is substituted with hydrogen or $C_1$–$C_6$ alkyl; $QR^5$ wherein Q is —O— or S(O)$_m$— and $R^5$ is selected from $C_1$–$C_6$ alkyl, $C_1$–$C_6$ haloalkyl, cyano-$C_1$–$C_6$-alkyl, $C_1$–$C_6$ alkoxycarbonyl-$C_1$–$C_6$-alkyl, $C_2$–$C_4$ alkenyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino;

$R^1$ is halogen, hydrogen, nitro, $C_1$–$C_6$ haloalkyl or $C_1$–$C_6$ alkyl-S(O)$_n$—, wherein n is 1 or 2;

R$^2$ is hydrogen, halogen, nitro, C$_1$–C$_6$ haloalkyl or C$_1$–C$_6$ alkyl-S(O)$_n$—, wherein n is 1 or 2;

R$^3$ is hydrogen; and

R$^4$ is hydrogen, halogen or C$_1$–C$_6$ haloalkyl.

21. A composition in accordance with claim 20 wherein

R is halogen; cyano; substituted amino wherein the substitutent(s) are selected from C$_1$–C$_6$ alkyl, C$_1$–C$_6$ alkoxy, hydroxy, formyl, C$_1$–C$_6$ alkylcarbonyl, C$_1$–C$_6$ alkoxycarbonyl, C$_1$–C$_6$ alkoxycarbonyl-C$_1$–C$_6$-alkylidenecarbonyl, hydroxycarbonyl-C$_1$–C$_6$-alkylidenecarbonyl, C$_1$–C$_6$ alkylsulfonyl, C$_1$–C$_6$ haloalkylsulfonyl, aminocarbonyl, (di)C$_1$–C$_6$-alkylaminocarbonyl, amino and (di)C$_1$–C$_6$-alkylamino; QR$^5$ wherein Q is —O— or —S— and R$^5$ is selected from C$_1$–C$_6$ alkyl, cyano-C$_1$–C$_6$-alkyl, C$_1$–C$_6$ alkoxycarbonyl-C$_1$–C$_6$-alkyl, C$_3$–C$_6$ alkynyl, hydroxycarbonyl-C$_1$–C$_6$-alkyl and aminocarbonyl-C$_1$–C$_6$-alkyl wherein the nitrogen atom may be optionally substituted with C$_1$–C$_6$ alkyl, C$_1$–C$_6$ alkoxy, C$_1$–C$_6$ alkylsulfonyl, C$_1$–C$_6$ haloalkylsulfonyl, amino or (di)C$_1$–C$_6$-alkylamino;

R$^1$ is chloro or fluoro;

R$^2$ is trifluoromethyl;

R$^3$ is hydrogen, and

X is N or C—H, C—Cl or C—F.

22. A composition in accordance with claim 16 wherein said compound is 4-chloro-1-(2-chloro-4-trifluoromethylphenyl)-pyrrolo [3,2-c]pyridine.

23. A composition in accordance with claim 16 wherein said compound is 4-chloro-1-(2-chloro-4-trifluoromethylphenyl)-pyrrolo [3,2-c]pyridine 5-oxide.

24. A composition in accordance with claim 16 wherein said compound is 1-(2-chloro-4-trifluoromethylphenyl)-4-methoxy-pyrrolo [3,2-c]pyridine.

25. A composition in accordance with claim 16 wherein said compound is 4-chloro-1-(3'-chloro-5'-trifluoromethylpyridin-2 '-yl)-pyrrolo [3,2-c]pyridine.

26. A composition in accordance with claim 16 wherein said compound is 4-chloro-1-(3'-chloro-5'-trifluoromethylpyridin-2-yl)-pyrrolo [3,2-c]pyridine 5-oxide.

27. A composition in accordance with claim 16 wherein said compound is 4-chloro-1-(2',6'-dichloro-4'-trifluoromethylphenyl)-pyrrolo [3,2-c]pyridine.

28. A composition in accordance with claim 16 wherein said compound is 4-methoxy-1-(2,',6'-dichloro-4'-trifluoromethylphenyl)-pyrrolo [3,2-c]pyridine.

29. A composition in accordance with claim 16 wherein said compound is 1—(2'-chloro-4'-trifluoromethylphenyl)-4-cyanopyrrolo [3,2-c]pyridine.

30. A composition in accordance with claim 16 wherein said compound is 1-2',6'-dichloro-4'-trifluoromethylphenyl)-4-cyanopyrrolo [3,2-c]pyridine.

31. A method for controlling undesirable vegetation comprising applying to the area where control is desired an herbicidally effective amount of a compound of the formula:

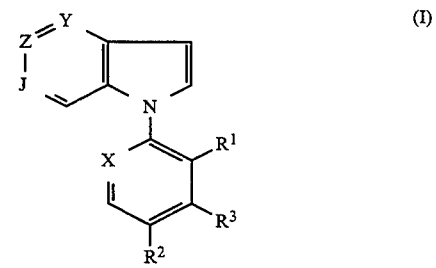

in which only one of Y, Z or J is N or N—O and the remainder of Y, Z or J is C—R wherein R is hydrogen; halogen; cyano; C$_1$–C$_6$ alkyl; C$_1$–C$_6$ haloalkyl; C$_1$–C$_6$ alkoxy-C$_1$–C$_6$-alkyl; formyl; C$_1$–C$_6$ alkylcarbonyl; C$_1$–C$_6$ alkylcarbonyloxy; carboxy and its salts, esters and amides thereof; amino; substituted amino wherein the substituent(s) are selected from C$_1$–C$_6$ alkyl, C$_1$–C$_6$ alkoxy, hydroxy, formyl, C$_1$–C$_6$ alkylcarbonyl, C$_1$–C$_6$ alkoxycarbonyl, C$_1$–C$_6$ alkoxycarbonyl-C$_1$–C$_6$-alkylidenecarbonyl, hydroxycarbonyl-C$_1$–C$_6$-alkylidenecarbonyl, C$_1$–C$_6$ alkylsulfonyl, C$_1$–C$_6$ haloalkylsulfonyl, aminocarbonyl, (di)C$_1$–C$_6$-alkylaminocarbonyl, amino and (di)C$_1$–C$_6$-alkylamino; sulfonamido wherein the N is substituted with hydrogen or C$_1$–C$_6$ alkyl; QR$^5$ wherein Q is —O— or s(O)$_m$— and R$^5$ is selected from hydrogen, C$_1$–C$_6$ alkyl, C$_1$–C$_6$ haloalkyl, cyano-C$_1$–C$_6$-alkyl, C$_1$–C$_6$ alkoxycarbonyl-C$_1$–C$_6$-alkyl, C$_2$–C$_4$ alkenyl, C$_3$–C$_6$ alkynyl, hydroxycarbonyl-C$_1$–C$_6$-alkyl and aminocarbonyl-C$_1$–C$_6$-alkyl wherein the nitrogen atom may be optionally substituted with C$_1$–C$_6$ alkyl, C$_1$–C$_6$ alkoxy, C$_1$–C$_6$ alkylsulfonyl, C$_1$–C$_6$ haloalkylsulfonyl, amino or (di)C$_1$–C$_6$ alkylamino;

R$^1$ is hydrogen, nitro, halogen, cyano, C$_1$–C$_6$ alkyl-S(O)$_m$— or C$_1$–C$_6$ alkoxy;

R$^2$ is halogen, C$_1$–C$_6$ haloalkyl, cyano, or C$_1$–C$_6$ alkyl-S(O)$_m$—;

R$^3$ is hydrogen or halogen;

X is N or C—R$^4$;

wherein R$^4$ is hydrogen, C$_1$–C$_6$ haloalkyl, halogen, cyano, nitro, C$_1$–C$_6$ alkyl-S(O)$_m$—or C$_1$–C$_6$ alkoxy;

m is 0, 1, 2; and agriculturally acceptable salts thereof.

32. A method in accordance with claim 31 wherein said compound is applied preemergently.

33. A method in accordance with claim 31 wherein said compound is applied postemergently.

34. A method in accordance with 31 wherein

R is halogen; cyano; C$_1$–C$_6$ alkyl; C$_1$–C$_6$ haloalkyl; C$_1$–C$_6$ alkylcarbonyl; C$_1$–C$_6$ alkylcarbonyloxy; substituted amino wherein the substituent(s) are selected from C$_1$–C$_6$ alkyl, C$_1$–C$_6$ alkoxy, hydroxy, formyl, C$_1$–C$_6$ alkylcarbonyl, C$_1$–C$_6$ alkoxycarbonyl, C$_1$–C$_6$ alkoxycarbonyl-C$_1$–C$_6$-alkylidenecarbonyl, hydroxycarbonyl-C$_1$–C$_6$-alkylidenecarbonyl, C$_1$–C$_6$ alkylsulfonyl, C$_1$–C$_6$ haloalkylsulfonyl, aminocarbonyl, (di)C$_1$–C$_6$-alkylaminocarbonyl, amino and (di)C$_1$–C$_6$-alkylamino; sulfonamido wherein the N is substituted with hydrogen or C$_1$–C$_6$ alkyl; QR$^5$ wherein Q is —O— or S(O)$_m$— and R$^5$ is selected from C$_1$–C$_6$ alkyl, C$_1$–C$_6$ haloalkyl, cyano-C$_1$–C$_6$-alkyl, C$_1$–C$_6$ alkoxycarbonyl-C$_1$–C$_6$-alkyl, C$_2$–C$_4$ alkenyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino.

35. A method in accordance with claim 31 wherein R is halogen; cyano; substituted amino wherein the substitutent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; $QR^5$ wherein Q is —O— or —S— and $R^5$ is selected from $C_1$–$C_6$ alkyl, cyano-$C_1$–$C_6$-alkyl, $C_1$–$C_6$ alkoxycarbonyl-$C_1$–$C_6$-alkyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino.

36. A method in accordance with claim 31 wherein
$R^1$ is chloro or fluoro;
$R^2$ is trifluoromethyl;
$R^3$ is hydrogen, and
X is N or C—H, C—Cl or C—F.

37. A method in accordance with claim 31 wherein R is halogen; cyano; $C_1$–$C_6$ alkyl; $C_1$–$C_6$ haloalkyl; $C_1$–$C_6$ alkylcarbonyl; $C_1$–$C_6$ alkylcarbonyloxy; substituted amino wherein the substituent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; sulfonamido wherein the N is substituted with hydrogen or $C_1$–$C_6$ alkyl; $QR^5$ wherein Q is —O— or $S(O)_m$— and $R^5$ is selected from $C_1$–$C_6$ alkyl, $C_1$–$C_6$ haloalkyl, cyano-$C_1$–$C_6$-alkyl, $C_1$–$C_6$ alkoxycarbonyl-$C_1$–$C_6$-alkyl, $C_2$–$C_4$ alkenyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino;
$R^1$ is halogen, hydrogen, nitro, $C_1$–$C_6$ haloalkyl or $C_1$–$C_6$ alkyl-$S(O)_n$—, wherein n is 1 or 2;
$R^2$ is hydrogen, halogen, nitro, $C_1$–$C_6$ haloalkyl or $C_1$–$C_6$ alkyl-$S(O)_n$—, wherein n is 1 or 2;
$R^3$ is hydrogen; and
$R^4$ is hydrogen, halogen or $C_1$–$C_6$ haloalkyl.

38. A method in accordance with claim 31 wherein R is halogen; cyano; substituted amino wherein the substitutent(s) are selected from $C_1$–$C_6$ alkyl, $C_1$–$C_6$ alkoxy, hydroxy, formyl, $C_1$–$C_6$ alkylcarbonyl, $C_1$–$C_6$ alkoxycarbonyl, $C_1$–$C_6$ alkoxycarbonyl-$C_1$–$C_6$-alkylidenecarbonyl, hydroxycarbonyl-$C_1$–$C_6$-alkylidenecarbonyl, $C_1$–$C_6$ alkylsulfonyl, $C_1$–$C_6$ haloalkylsulfonyl, aminocarbonyl, (di)$C_1$–$C_6$-alkylaminocarbonyl, amino and (di)$C_1$–$C_6$-alkylamino; $QR^5$ wherein Q is —O— or —S— and $R^5$ is selected from $C_1$–$C_6$ alkyl, cyano-$C_1$–$C_6$-alkyl, $C_1$–$C_6$ alkoxycarbonyl-$C_1$–$C_6$-alkyl, $C_3$–$C_6$ alkynyl, hydroxycarbonyl-$C_1$–$C_6$-alkyl and aminocarbonyl-$C_1$–$C_6$-alkyl wherein the nitrogen atom may be optionally substituted with $C_1$–$C_6$ alkyl, $C_1$–$C_6$ alkoxy, $C_1$–$C_6$ alkylsulfonyl, $C_1$–$C_6$ haloalkylsulfonyl, amino or (di)$C_1$–$C_6$-alkylamino;
$R^1$ is chloro or fluoro;
$R^2$ is trifluoromethyl;
$R^3$ is hydrogen, and
X is N or C—H, C—Cl or C—F.

39. A method in accordance with claim 31 wherein said compound is 4-chloro-1-(2-chloro-4-trifluoromethylphenyl)-pyrrolo [3,2-c]pyridine.

40. A method in accordance with claim 31 wherein said compound is 4-chloro-1-(2-chloro-4-trifluoromethylphenyl)pyrrolo [3,2-c]pyridine 5-oxide.

41. A method in accordance with claim 31 wherein said compound is 1-(2-chloro-4-trifluoromethylphenyl)-4-methoxy-pyrrolo [3,2-c]pyridine.

42. A method in accordance with claim 31 wherein said compound is 4-chloro-1-(3'-chloro-5'-trifluoromethylpyridin-2 '-yl)-pyrrolo [3,2-c]pyridine.

43. A method in accordance with claim 31 wherein said compound is 4 -chloro-1-(3'-chloro-5'-trifluoromethylpyridin-2-yl)-pyrrolo [3,2-c]pyridine 5-oxide.

44. A method in accordance with claim 31 wherein said compound is 4-chloro-1-(2',6'-dichloro-4'-trifluoromethylphenyl)-pyrrolo [3,2-c]pyridine.

45. A method in accordance with claim 31 wherein said compound is 4-methoxy-1-(2,',6'-dichloro-4'-trifluoromethylphenyl)-pyrrolo [3,2-c]pyridine.

46. A method in accordance with claim 31 wherein said compound is 1-(2'-chloro-4'-trifluoromethylphenyl)-4-cyanopyrrolo [3,2-c]pyridine.

47. A method in accordance with claim 31 wherein said compound is 1—2',6'-dichloro-4'-trifluoromethylphenyl)-4-cyanopyrrolo [3,2-c]pyridine.

* * * * *